(12) United States Patent
An et al.

(10) Patent No.: US 9,315,870 B2
(45) Date of Patent: Apr. 19, 2016

(54) METHOD FOR DETECTING METHYLATION OF COLORECTAL CANCER SPECIFIC METHYLATION MARKER GENE FOR COLORECTAL CANCER DIAGNOSIS

(75) Inventors: Sung Whan An, Daejeon (KR); Tae Jeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 214 days.

(21) Appl. No.: 13/994,732

(22) PCT Filed: Dec. 16, 2011

(86) PCT No.: PCT/KR2011/009710
§ 371 (c)(1),
(2), (4) Date: Oct. 22, 2013

(87) PCT Pub. No.: WO2012/081928
PCT Pub. Date: Jun. 21, 2012

(65) Prior Publication Data
US 2014/0045180 A1 Feb. 13, 2014

(30) Foreign Application Priority Data

Dec. 16, 2010 (KR) .......................... 10-2010-0129208

(51) Int. Cl.
C07H 21/04 (2006.01)
C12Q 1/68 (2006.01)
C07K 14/705 (2006.01)

(52) U.S. Cl.
CPC ............ *C12Q 1/6886* (2013.01); *C07K 14/705* (2013.01); *C12Q 2600/154* (2013.01)

(58) Field of Classification Search
None
See application file for complete search history.

(56) References Cited

U.S. PATENT DOCUMENTS

| 5,474,796 A * | 12/1995 | Brennan ........................ 427/2.13 |
| 5,786,146 A | 7/1998 | Herman et al. |
| 2012/0101023 A1* | 4/2012 | Zwarthoff ............ C12Q 1/6886 514/1.1 |
| 2012/0264640 A1* | 10/2012 | An .......................... C12Q 1/686 506/9 |

FOREIGN PATENT DOCUMENTS

| EP | 1862555 | * 12/2007 | ................ C12Q 1/68 |
| WO | WO 2010/123354 | * 10/2010 | ................ C12Q 1/68 |

OTHER PUBLICATIONS

Shimizu et al. (Cytogenetic Cell Genet. vol. 74, pp. 138-139, 1996).*
Gitan et al. (Genome Research, vol. 12, pp. 158-164, 2001).*
Alfonso, J., et al., "The stress-regulated protein M6a is a key modulator for neurite outgrowth and filopodium/spine formation", "Proceedings of National Academy of Sciences", Nov. 22, 2005, pp. 17196-17201, vol. 102, No. 47.
Kimura, N., et al., "Methylation profiles of genes utilizing newly developed CpG island methylation microarray on colorectal cancer patients", "Nucleic acids research", 2005, p. e46, vol. 33, No. 5.
Mukobata, S., et al., "M6a acts as a nerve growth factor-gated Ca2+ channel in neuronal differentiation", "Biochemical and Biophysical Research Communications", 2002, pp. 722-728, vol. 297.
Toyota, M., et al., "Identification of differentially methylated sequences in colorectal cancer by methylated CpG island amplification", "Cancer Research", May 15, 1999, pp. 2307-2312, vol. 59.
Ahlquist, D., et al., "Colorectal Cancer Screening by Detection of Altered Human DNA in Stool: Feasibility of a Multitarget Assay Panel", "Gastroenterology", Nov. 2000, pp. 1219-1227, vol. 119, No. 5.
Chen, X., et al., "Detecting tumor-related alterations in plasma or serum DNA of patients diagnosed with breast cancer", "Clin Cancer Res.", Sep. 1999, pp. 2297-2303, vol. 5, No. 9.
Esteller, M., et al., "Detection of Aberrant Promoter Hypermethylation of Tumor Suppressor Genes in Serum DNA from Non-Small Cell Lung Cancer Patients", "Cancer Research", Jan. 1, 1999, pp. 67-70, vol. 59.
Fraga, M., et al., "The affinity of different MBD proteins for a specific methylated locus depends on their intrinsic binding properties", "Nucleic Acids Research", Mar. 15, 2003, pp. 1765-1774, vol. 31, No. 6.
Goessl, C., et al., "Fluorescent Methylation-specific Polymerase Chain Reaction for DNA-based Detection of Prostate Cancer in Bodily Fluids", "Cancer Research", Nov. 1, 2000, pp. 5941-5945, vol. 60.
Kopreski, M., et al., "Detection of Tumor Messenger RNA in the Serum of Patients with Malignant Melanoma", "Clinical Cancer Research", Aug. 1999, pp. 1961-1965, vol. 5.
Malik, K., et al., "Epigenetic gene deregulation in cancer", "British Journal of Cancer", Dec. 2000, pp. 1583-1588, vol. 83, No. 12.
Miyashiro, I., et al., "Molecular Strategy for Detecting Metastatic Cancers with Use of Multiple Tumor-specific MAGE-A Genes", "Clinical Chemistry", Mar. 2001, pp. 505-512, vol. 47, No. 3.
Palmisano, W., et al., "Predicting Lung Cancer by Detecting Aberrant Promoter Methylation in Sputum", "Cancer Research", Nov. 1, 2000, pp. 5954-5958, vol. 60.

(Continued)

*Primary Examiner* — Jeanine A Goldberg
(74) *Attorney, Agent, or Firm* — Hultquist, PLLC; Mary B. Grant

(57) ABSTRACT

The present invention relates to a method for detecting methylation of the bowel-cancer-specific methylation marker GPM6A (NM_201591, glycoprotein M6A) gene in order to diagnose bowel cancer, and more specifically relates to a method for providing information for diagnosing bowel cancer by detecting the methylation of a bowel-cancer-specific marker gene that is specifically methylated in bowel cancer cells. The method for detecting methylation and a diagnostic composition, kit and nucleic-acid chip according to the present invention can be used to advantage in diagnosing bowel cancer more accurately and quickly than by normal methods as they permit bowel cancer to be diagnosed at the initial genetic transformation step and so allow early diagnosis.

10 Claims, 4 Drawing Sheets

(56) References Cited

OTHER PUBLICATIONS

Robertson, K., et al, "DNA Methylation: past, present and future directions", "Carcinogenesis", Mar. 2000, pp. 461-467, vol. 21, No. 3.

Sanchez-Cespedes, M., et al., "Gene Promoter Hypermethylation in Tumors and Serum of Head and Neck Cancer Patients", "Cancer Research", Feb. 15, 2000, pp. 892-895, vol. 60.

Singal, R., et al., "DNA Methylation", "Blood", Jun. 15, 1999, pp. 4059-4070, vol. 93, No. 12.

Sozzi, G., et al., "Detection of Microsatellite Alterations in Plasma DNA of Non-Small Cell Lung Cancer Patients: A Prospect for Early Diagnosis", "Clinical Cancer Research", Oct. 1999, pp. 2689-2692, vol. 5.

Sueoka, E., et al., "Heterogeneous Nuclear Ribonucleoprotein B1 as a New Marker of Early Detection for Human Lung Cancers", "Cancer Research", Apr. 1, 1999, pp. 1404-1407, vol. 59.

\* cited by examiner

METHOD FOR DETECTING METHYLATION OF COLORECTAL CANCER SPECIFIC METHYLATION MARKER GENE FOR COLORECTAL CANCER DIAGNOSIS

CROSS-REFERENCE TO RELATED APPLICATIONS

This application is a U.S. national phase under the provisions of 35 U.S.C. §371 of International Patent Application No. PCT/KR11/09710 filed Dec. 16, 2011, which in turn claims priority under 35 U.S.C. §119 of Korean Patent Application No. 10-2010-129208 filed Dec. 16, 2010. The disclosures of such international patent application and Korean priority patent application are hereby incorporated herein by reference in their respective entireties, for all purposes.

TECHNICAL FIELD

The present invention relates to a method for detecting the methylation of colorectal cancer-specific marker genes for colorectal cancer diagnosis, and more particularly to a method of detecting the methylation of a colorectal cancer-specific marker gene, which are methylated specifically in colorectal cancer cells, to provide information for diagnosing colorectal cancer.

BACKGROUND ART

In current clinical practice, the diagnosis of cancer is confirmed by performing tissue biopsy after history taking, physical examination and clinical assessment, followed by radiographic testing and endoscopy if cancer is suspected. However, the diagnosis of cancer by the existing clinical practices is possible only when the number of cancer cells is more than a billion and the diameter of cancer is more than 1 cm. In this case, the cancer cells already have metastatic ability, and at least half thereof have already metastasized. Meanwhile, tumor markers for monitoring substances that are directly or indirectly produced from cancers are used in cancer screening, but they cause confusion due to limitations in accuracy, since up to about half thereof appear normal even in the presence of cancer, and they often appear positive even in the absence of cancer. Furthermore, the anticancer agents that are mainly used in cancer therapy have the problem that they show an effect only when the volume of cancer is small.

Recently, genetic analysis has been actively attempted to diagnose cancer. The simplest typical method is to detect the presence of ABL: BCR fusion genes (the genetic characteristic of leukemia) in blood by PCR. The method has an accuracy rate of more than 95%, and after the diagnosis and therapy of chronic myelocytic leukemia using this simple and easy genetic analysis, this method is being used for the assessment of the result and follow-up study. However, this method has a shortcoming in that it can be applied only to some blood cancers.

Furthermore, another method has been attempted, in which the presence of genes expressed by cancer cells is detected by RT-PCR and blotting, thereby diagnosing cancer cells present in blood cells. However, this method has shortcomings in that it can be applied only to some cancers, including prostate cancer and melanoma, has a high false positive rate. In addition, it is difficult to standardize detection and reading in this method, and its utility is also limited (Kopreski, M. S. et al., *Clin. Cancer Res.*, 5:1961, 1999; Miyashiro, I. et al., *Clin. Chem.*, 47:505, 2001).

Recently, genetic testing that uses a DNA in serum or blood plasma has been actively attempted. This is a method of detecting a cancer-related gene that is isolated from cancer cells and released into blood and present in the form of a free DNA in serum. It is found that the concentration of DNA in serum is increased by a factor of 5-10 times in actual cancer patients as compared to that of normal persons, and such increased DNA is released mostly from cancer cells. The analysis of cancer-specific gene abnormalities, such as the mutation, deletion and functional loss of oncogenes and tumor-suppressor genes, using such DNAs isolated from cancer cells, allows the diagnosis of cancer. In this effort, there has been an active attempt to diagnose lung cancer, head and neck cancer, breast cancer, colorectal cancer, and liver cancer by examining the promoter methylation of mutated K-Ras oncogenes, p53 tumor-suppressor genes and p16 genes in serum, and the labeling and instability of microsatellite (Chen, X. Q. et al., *Clin. Cancer Res.*, 5:2297, 1999; Esteller, M. et al., *Cancer Res.*, 59:67, 1999; Sanchez-Cespedes, M. et al., *Cancer Res.*, 60:892, 2000; Sozzi, G. et al., *Clin. Cancer Res.*, 5:2689, 1999).

Meanwhile, in samples other than blood, the DNA of cancer cells can also be detected. A method has been attempted in which the presence of cancer cells or oncogenes in sputum or bronchoalveolar lavage of lung cancer patients is detected by a gene or antibody test (Palmisano, W. A. et al., *Cancer Res.*, 60:5954, 2000; Sueoka, E. et al., *Cancer Res.*, 59:1404, 1999). Additionally, other methods of detecting the presence of oncogenes in feces of colorectal cancer patients (Ahlquist, D. A. et al., *Gastroenterol.*, 119:1219-27, 2000) and detecting promoter methylation abnormalities in urine and prostate fluid (Goessl, C. et al., *Cancer Res.*, 60:5941, 2000) have been attempted. However, in order to accurately diagnose cancers that cause a large number of gene abnormalities and show various mutations characteristic of each cancer, a method in which a large number of genes are simultaneously analyzed in an accurate and automatic manner is required. However, such a method has not yet been established.

Accordingly, methods of diagnosing cancer by measuring DNA methylation have recently been proposed. When the promoter CpG island of a certain gene is hyper-methylated, the expression of such a gene is silenced. This is interpreted to be a main mechanism by which the function of this gene is lost even when there is no mutation in the protein-coding sequence of the gene in a living body. In addition, this is analyzed as a factor by which the function of a number of tumor-suppressor genes in human cancer is lost. Thus, analysis of the methylation of the promoter CpG island of tumor-suppressor genes is very helpful in cancer research. An active attempt has been made to analyze the methylation of the promoter CpG island by methods such as methylation-specific PCR (hereinafter, referred to as "MSP") or automatic base sequencing and to use the analysis results for the diagnosis and screening of cancer.

A significant number of diseases are caused by genetic abnormalities, and the most frequent form of genetic abnormality is a change in the coding sequence of a gene. This genetic change is referred to as mutation. When any gene has a mutation, the structure and function of a protein encoded by the gene change, resulting in abnormalities and deletions, and this mutant protein causes disease. However, an abnormality in the expression of a specific gene can cause disease even in the absence of a mutation in the gene. A typical example thereof is methylation in which a methyl group is attached to the transcription regulatory region of a gene, that is, the cytosine base of the promoter CpG islands, and in this case, the expression of the gene is silenced. This is known as epigenetic change. This is transmitted to offspring and results in the loss of the expression of the relevant protein in the same manner as mutation. Most typically, the expression of tumor suppressor genes is silenced by the methylation of promoter CpG islands in cancer cells, resulting in carcinogenesis (Robertson, K. D. et al., *Carcinogensis*, 21:461, 2000).

During a cancer-causing process, methylation is found in promoter CpG islands, and the restriction on the corresponding gene expression occurs. Particularly, if methylation occurs in the promoter CpG islands of tumor-suppressor genes that regulate cell cycle or apoptosis, restore DNA, are involved in the adhesion of cells and the interaction between cells, and/or suppress cell invasion and metastasis, such methylation blocks the expression and function of such genes in the same manner as the mutations of a coding sequence, thereby promoting the development and progression of cancer. In addition, partial methylation also occurs in the CpG islands according to aging.

An interesting fact is that, in the case of genes whose mutations are attributed to the development of cancer in congenital cancer but do not occur in acquired cancer, the methylation of promoter CpG islands occurs instead of mutation. Typical examples include the promoter methylation of genes, such as acquired renal cancer VHL (von Hippel Lindau), breast cancer BRCA1, colorectal cancer MLH1, and stomach cancer E-CAD. In addition, in about half of all cancers, the promoter methylation of p16 or the mutation of Rb occurs, and the remaining cancers show the mutation of p53 or the promoter methylation of p73, p 14 and the like.

An important fact is that an epigenetic change caused by promoter methylation causes a genetic change (i.e., the mutation of a coding sequence), and the development of cancer is progressed by the combination of such genetic and epigenetic changes. In a MLH1 gene as an example, there is the circumstance in which the function of one allele of the MLH1 gene in colorectal cancer cells is lost due to its mutation or deletion, and the remaining one allele does not function due to promoter methylation. In addition, if the function of MLH1, which is a DNA restoring gene, is lost due to promoter methylation, the occurrence of mutation in other important genes is facilitated to promote the development of cancer.

Most cancers show three common characteristics with respect to CpG, namely, hypermethylation of the promoter CpG islands of tumor-suppressor genes, hypomethylation of the remaining CpG base sites, and an increase in the activity of methylation enzyme, namely, DNA cytosine methyltransferase (DNMT) (Singal, R. & Ginder, G. D., *Blood*, 93:4059, 1999; Robertson, K. et al., *Carcinogensis*, 21:461, 2000; Malik, K. & Brown, K. W., *Brit. J. Cancer*, 83:1583, 2000).

When promoter CpG islands are methylated, the reason why the expression of the corresponding genes is blocked is not clearly established, but is presumed to be because a methyl CpG-binding protein (MECP) or a methyl CpG-binding domain protein (MBD), and histone deacetylase, bind to methylated cytosine, thereby causing a change in the chromatin structure of chromosomes and a change in histone protein.

It is unsettled whether the methylation of promoter CpG islands directly causes the development of cancer or is a secondary change after the development of cancer. However, it is clear that the promoter methylation of tumor-related genes is an important index to cancer, and thus can be used in many applications, including the diagnosis and early detection of cancer, the prediction of the risk of the development of cancer, the prognosis of cancer, follow-up examination after treatment, and the prediction of a response to anticancer therapy. Recently, an attempt to examine the promoter methylation of tumor-related genes in blood, sputum, saliva, feces or urine and to use the examined results for the diagnosis and treatment of various cancers, has been actively conducted (Esteller, M. et al., *Cancer Res.*, 59:67, 1999; Sanchez-Cespedez, M. et al., *Cancer Res.*, 60:892, 2000; Ahlquist, D. A. et al., *Gastroenterol.*, 119:1219, 2000).

In order to maximize the accuracy of cancer diagnosis using promoter methylation, analyze the development of cancer according to each stage and discriminate a change according to cancer and aging, an examination that can accurately analyze the methylation of all the cytosine bases of promoter CpG islands is required. Currently, a standard method for this examination is a bisulfite genome-sequencing method, in which a sample DNA is treated with sodium bisulfite, and all regions of the CpG islands of a target gene to be examined is amplified by PCR, and then, the base sequence of the amplified regions is analyzed. However, this examination has the problem that there are limitations to the number of genes or samples that can be examined at a given time. Other problems are that automation is difficult, and much time and expense are required.

In the Johns Hopkins School of Medicine, the MD Anderson Cancer Center, Charité-Universitätsmedizin Berlin, etc., studies on promoter methylation of cancer-related genes have been actively conducted. The fundamental data thus obtained are interchanged through the DNA Methylation Society (DMS) and stored in MethDB (http://www.methdb.de). Meanwhile, EpiGenX Pharmaceuticals, Inc. is now developing therapeutic agents associated with the methylation of CpG islands, and Epigenomics, Inc. is now conducting studies to apply promoter methylation to cancer diagnosis by examining the promoter methylation using various techniques, such as DNA chips and MALDI-TOF.

Accordingly, the present inventors have made extensive efforts to develop an effective colon-cancer-specific methylation marker which makes it possible to diagnose cancer and the risk of carcinogenesis at an early stage and predict cancer prognosis. As a result, the present inventors have found that GPM6A (NM_005277, Glycoprotein M6A) gene is methylated specifically in colorectal cancer cells and that colorectal cancer can be diagnosed by measuring the degree of methylation using this gene as a biomarker, thereby completing the present invention.

DISCLOSURE OF INVENTION

It is a main object of the present invention to provide a colorectal cancer-specific methylation biomarker, which is methylated specifically in colorectal cancer cells and can be effectively used for diagnosis of colorectal cancer.

Another object of the present invention is to provide a method for detecting colorectal cancer, the method comprising identifying the degree of methylation of the biomarker.

Still another object of the present invention is to provide a nucleic acid chip for diagnosing colorectal cancer, which comprises a probe capable of hybridizing with a fragment comprising the CpG island of the colorectal cancer-specific methylation biomarker.

To achieve the above objects, the present invention provides a biomarker for diagnosing colorectal cancer, which comprises either the methylated CpG island of the promoter of GPM6A (NM_201591, glycoprotein M6A) gene or the methylated CpG island of a first intron of GPM6A (NM_201591, glycoprotein M6A) gene.

The present invention also provides a method for detecting the methylation of a biomarker for colorectal cancer diagnosis, the method comprising the steps of:

(a) isolating DNAs from a clinical sample;
(b) detecting the methylation of the CpG island of the promoter of GPM6A (NM_201591, glycoprotein M6A) gene or the CpG island of a first intron of GPM6A (NM_201591, glycoprotein M6A) gene from the isolated DNAs.

The present invention also provides a nucleic acid chip for diagnosing colorectal cancer, which comprises a probe capable of hybridizing with a fragment comprising either the CpG island of the promoter of GPM6A (NM_201591, glycoprotein M6A) gene or the CpG island of a first intron of GPM6A (NM_201591, glycoprotein M6A) gene.

The present invention also provides a kit for diagnosing colorectal cancer, which contains: a PCR primer pair for amplifying a fragment comprising the methylated CpG island of a first intron of GPM6A (NM_201591, glycoprotein M6A) gene; and a sequencing primer for pyrosequencing a PCR product amplified by the primer pair.

Other features and embodiments of the present invention will be more apparent from the following detailed descriptions and the appended claims

BEST MODE FOR CARRYING OUT THE INVENTION

Figure 1:
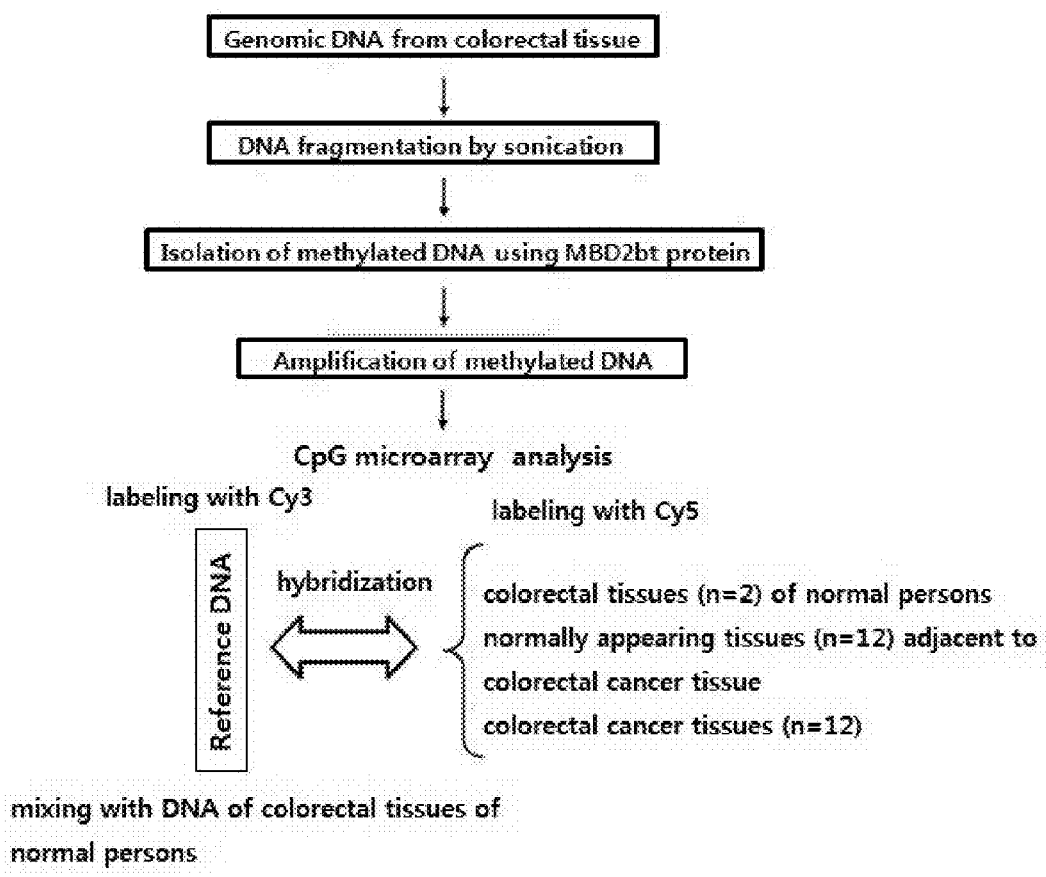
FIG. 1 is a schematic diagram showing a process of discovering a methylation biomarker for colorectal cancer diagnosis from the tissue cells of a normal person and a colorectal cancer patient by a CpG microassay.

Unless defined otherwise, all technical and scientific terms used herein have the same meaning as commonly understood by one of ordinary skill in the art to which the invention pertains. Generally, the nomenclature used herein are well known and are commonly employed in the art.

In one aspect, the present invention is directed to a biomarker for diagnosing colorectal cancer, which comprises either the methylated CpG island of the promoter of GPM6A (NM_201591, glycoprotein M6A) gene or the methylated CpG island of a first intron of GPM6A (NM_201591, glycoprotein M6A) gene.

In the present invention, the CpG island may be located in the intron region of the gene. Herein, the intron region of the GPM6A gene may be located between +501 and +1200 nucleotides (nt) from the transcription start site and may comprise a nucleotide sequence of SEQ ID NO: 1.

In another aspect, the present invention is directed to a method for detecting the methylation of a biomarker for colorectal cancer diagnosis, the method comprising the steps of:

(a) isolating DNA from a clinical sample;
(b) detecting the methylation of the CpG island of the promoter of GPM6A (NM_201591, glycoprotein M6A) gene or the CpG island of a first intron of GPM6A (NM_201591, glycoprotein M6A) gene from the isolated DNA.

In the present invention, step (b) of detecting the methylation of the CpG island of a first intron of GPM6A (NM_201591, glycoprotein M6A) gene may be performed by detecting the methylation of the region shown by SEQ ID NO: 1.

In the present invention, step (b) may be performed by detecting the methylation based on the presence/absence or a change in the base sequence of product amplified by using primers capable of amplifying a fragment comprising the CpG island of the first intron of GPM6A (NM_201591, glycoprotein M6A) gene.

In the present invention, step (b) may be performed by a method selected from the group consisting of PCR, methylation-specific PCR, real-time methylation-specific PCR, PCR assay using a methylation DNA-specific binding protein, quantitative PCR, DNA chip-based assay, pyrosequencing, and bisulfate sequencing.

In the present invention, the clinical sample may be selected from the group consisting of a tissue, cell, blood, blood plasma, feces, and urine from a patient suspected of cancer or a subject to be diagnosed.

In the present invention, 4 biomarker candidate genes showing the greatest difference in the degree of methylation between normal persons and colorectal cancer patients were screened, and among these genes, SDC2, SIM1 and SORCS3 genes were confirmed for diagnosis of colorectal cancer. A method for screening methylation marker genes according to the present invention comprises the steps of: (a) isolating genomic DNAs from transformed cells and non-transformed cells; (b) reacting the isolated genomic DNAs with a methylated DNA-binding protein, thereby isolating methylated DNAs; and (c) amplifying the methylated DNAs, hybridizing the amplified DNAs to a CpG microarray, and then selecting genes showing the greatest difference in the degree of methylation between the normal cells and the cancer cells, thereby ensuring methylation marker genes.

The above method for screening biomarker genes can find genes which are differentially methylated in colorectal cancer as well as at various dysplasic stages of the tissue that progresses to colorectal cancer. The screened genes can be used for colorectal cancer screening, risk-assessment, prognosis, disease identification, the diagnosis of disease stages, and the selection of therapeutic targets.

The identification of genes that are methylated in colorectal cancer and abnormalities at various stages of colorectal cancer makes it possible to diagnose colorectal cancer at an early stage in an accurate and effective manner and allows methylation profiling of multiple genes and the identification of new targets for therapeutic intervention. Furthermore, the methylation data according to the present invention may be combined with other non-methylation related biomarker detection methods to obtain a more accurate system for colorectal cancer diagnosis.

According to the method of the present invention, the progression of colorectal cancer at various stages or phases can be diagnosed by determining the methylation stage of one or more nucleic acid biomarkers obtained from a sample. By comparing the methylation stage of a nucleic acid isolated from a sample at each stage of colorectal cancer with the methylation stage of one or more nucleic acids isolated from a sample in which there is no cell proliferative disorder of colon tissue, a specific stage of colorectal cancer in the sample can be detected. Herein, the methylation stage may be hypermethylation.

In one embodiment of the present invention, nucleic acid may be methylated in the regulatory region of a gene. In another embodiment, a gene which is involved in cell transformation can be diagnosed by detecting methylation outside of the regulatory region of the gene, because methylation proceeds inwards from the outside of the gene.

In yet another embodiment of the present invention, cells that are likely to form colorectal cancer can be diagnosed at an early stage using the methylation marker genes. When genes confirmed to be methylated in cancer cells are methylated in cells that appear normal clinically or morphologically, this indicates that the normally appearing cells progress to cancer. Thus, colorectal cancer can be diagnosed at an early stage by detecting the methylation of colorectal cancer-specific genes in cells that appear normal.

The use of the methylation marker gene of the present invention allows for detection of a cellular proliferative disorder (dysplasia) of colon tissue in a sample. The detection method comprises bringing a sample comprising at least one nucleic acid isolated from a subject into contact with at least one agent capable of determining the methylation state of the nucleic acid. The method comprises detecting the methylation of at least one region in at least one nucleic acid, wherein the methylation of the nucleic acid differs from the methylation state of the same region of a nucleic acid present in a sample in which there is no abnormal growth (dysplastic progression) of colon cells.

In yet another embodiment of the present invention, the likelihood of progression of tissue to colorectal cancer can be evaluated by examining the frequency of the methylation of a gene which is specifically methylated in colorectal cancer, and determining the methylation frequency of tissue that is likely to progress to colorectal cancer.

Thus, in still another aspect, the present invention is directed to a method for detecting the methylation of colorectal cancer-specific methylation marker gene for colorectal cancer diagnosis, the method comprising the steps of:

(a) preparing a clinical sample containing DNA; and
(b) detecting the methylation of the CpG island of a first intron of GPM6A (NM_005277, glycoprotein M6A) gene in the DNA of the clinical sample.

In the present invention, step (b) may be performed by detecting the methylation of the CpG island in the intron region of the gene. Herein, the intron region of the GPM6A gene may be located between +501 and +1200 nucleotides (nt) from the transcription start site and may comprise a nucleotide sequence of SEQ ID NO: 1.

In the present invention, step (b) may be performed by a method selected from the group consisting of PCR, methylation-specific PCR, real-time methylation-specific PCR, PCR assay using a methylation DNA-specific binding protein, quantitative PCR, DNA chip-based assay, pyrosequencing, and bisulfate sequencing. In addition, the clinical sample may be selected from the group consisting of a tissue, cell, blood, blood plasma, feces, and urine from a patient suspected of cancer or a subject to be diagnosed, but is not limited thereto.

In one embodiment of the present invention, the method for detecting the methylation of a gene may comprise: (a) preparing a clinical sample containing DNA; (b) isolating DNA from the clinical sample; (c) amplifying the isolated DNA using primers capable of amplifying a fragment comprising the CpG island of a first intron of GPM6A (NM_005277, glycoprotein M6A) gene; and (d) determining whether the intron was methylated based on whether the DNA was amplified in step (c).

In yet another aspect, the present invention is directed to a nucleic acid chip for diagnosing colorectal cancer, which comprises a probe capable of hybridizing with a fragment comprising the CpG island of a first intron of GPM6A (NM_201591, glycoprotein M6A) gene.

In the present invention, the CpG island may be located in the intron region of the gene. Herein, the intron region of the GPM6A gene may be located between +501 and +1200 nucleotides (nt) from the transcription start site and may comprise a nucleotide sequence of SEQ ID NO: 1.

In a further another aspect, the present invention is directed to a kit for diagnosing colorectal cancer, which contains: a PCR primer pair for amplifying a fragment comprising the methylated CpG island of a first intron of GPM6A (NM_201591, glycoprotein M6A) gene; and a sequencing primer for pyrosequencing a PCR product amplified by the primer pair.

In the present invention, the PCR primer pair may be a primer pair comprising base sequences shown by SEQ ID NOS: 16 and 17 or SEQ ID NO: 18 and 19, and the sequencing primer may comprise a base sequence shown by SEQ ID NO: 15.

In yet another embodiment of the present invention, the abnormal growth (dysplasia) of colorectal tissue cells in a sample can be diagnosed by detecting the methylation state of CpG island of a first intron of GPM6A (NM_201591, glycoprotein M6A) gene using a kit.

In the present invention, the probe may be selected from the group consisting of the base sequences shown by SEQ ID NOS: 2 to 6, and specific examples thereof are as follows.

The probe capable of hybridizing with the CpG island of a first intron of GPM6A:

```
                                              (SEQ ID NO: 2)
1)    gtatttggga aataaagaaa (SEQ ID NO: 3)
2)    gactaagaga cccaggatcc gaatagcgag (SEQ ID NO: 4)
3)    gttcccacgt tttcatgttc tctttgggga gcaagttgaa (SEQ ID NO: 5)
4)    ggcgtccaca ctggctcggg tcactggacg gtggagttcg
      gcgcagttca (SEQ ID NO: 6)
5)    agtttccagg cagggtccgc ttattcggtg cttagcggag
      gcagcttgga atagctccag
```

The use of the diagnostic kit or nucleic acid chip of the present invention makes it possible to determine the abnormal growth (dysplastic progression) of colon tissue cells in a sample. The method comprises determining the methylation state of at least one nucleic acid isolated from a sample, wherein the methylation state of the at least one nucleic acid is compared with the methylation stage of a nucleic acid isolated from a sample in which there is no abnormal growth (dysplastic progression) of colorectal cells.

In another embodiment of the present invention, transformed colorectal cancer cells can be detected by examining the methylation of the marker gene using said nucleic acid chip.

In still another embodiment of the present invention, colorectal cancer can be diagnosed by examining the methylation of the marker gene using said nucleic acid chip.

In yet another embodiment of the present invention, the likelihood of progression to colorectal cancer can be diagnosed by examining the methylation of the marker gene in a sample showing a normal phenotype using said kit or nucleic acid chip. The sample that is used in the present invention may be solid or liquid tissue, cells, feces, urine, serum, or blood plasma.

Major terms which are used herein are defined as follows.

As used herein, the term "cell transformation" refers to the change in characteristics of a cell from one form to another form such as from normal to abnormal, non-tumorous to tumorous, undifferentiated to differentiated, stem cell to non-stem cell. In addition, the transformation can be recognized by the morphology, phenotype, biochemical characteristics and the like of a cell.

As used herein, the term "early detection" of cancer refers to discovering the likelihood of cancer prior to metastasis, and preferably before observation of a morphological change in a tissue or cell. Furthermore, the term "early detection" of cell transformation refers to the high probability of a cell to undergo transformation in its early stages before the cell is morphologically designated as being transformed.

As used herein, the term "hypermethylation" refers to the methylation of a CpG island.

As used herein, the term "sample" or "clinical sample" is referred to in its broadest sense, and includes any biological sample obtained from an individual, body fluid, a cell line, a tissue culture, depending on the type of assay that is to be performed. Methods for obtaining tissue biopsies and body fluids from mammals are well known in the art. A tissue biopsy of the colon is a preferred source.

Biomarker for Colorectal Cancer—Use of Cancer Cells for Comparison with Normal Cells In the present invention, "normal" cells refer to those that do not show any abnormal morphological or cytological changes. "Tumor" cells are cancer cells. "Non-tumor" cells are those cells that are part of the diseased tissue but are not considered to be the tumor portion.

In one aspect, the present invention is based on the discovery of the relationship between colorectal cancer and the hypermethylation of GPM6A (NM_005277, glycoprotein M6A) gene.

In another embodiment of the present invention, a cellular proliferative disorder of colorectal tissue cell can be diagnosed at an early stage by determining the methylation stage of at least one nucleic acid from a subject using the kit or nucleic acid chip of the present invention. Herein, the methylation stage of the at least one nucleic acid may be compared with the methylation state of at least one nucleic acid isolated from a subject not having a cellular proliferative disorder of colon tissue. The nucleic acid is preferably a CpG-containing nucleic acid such as a CpG island.

In another embodiment of the present invention, a cellular proliferative disorder of colon tissue can be diagnosed by determining the methylation of at least one nucleic acid from a subject using the kit or nucleic acid chip of the present invention. Herein, the nucleic acid may be a CpG island gene of GPM6A (NM_005277, glycoprotein M6A) gene. In this embodiment, the methylation of the at least one nucleic acid may be compared with the methylation state of at least one nucleic acid isolated from a subject having no predisposition to a cellular proliferative disorder of colon tissue.

As used herein, "predisposition" refers to the property of being susceptible to a cellular proliferative disorder. A subject having a predisposition to a cellular proliferative disorder has no cellular proliferative disorder, but is a subject having an increased likelihood of having a cellular proliferative disorder.

In another aspect, the present invention provides a method for diagnosing a cellular proliferative disorder of colon tissue, the method comprising brining a sample comprising a nucleic acid into contact with an agent capable of determining the methylation state of the sample, and determining the methylation of at least one region of the at least one nucleic acid. Herein, the methylation of the at least one region in the at least one nucleic acid differs from the methylation stage of the same region in a nucleic acid present in a subject in which there is no abnormal growth of cells.

The method of the present invention comprises a step of determining the methylation of at least one region of at least one nucleic acid isolated from a subject.

The term "nucleic acid" or "nucleic acid sequence" as used herein refers to an oligonucleotide, nucleotide or polynucleotide, or fragments thereof, or single-stranded or double-stranded DNA or RNA of genomic or synthetic origin, sense- or antisense-strand DNA or RNA of genomic or synthetic origin, peptide nucleic acid (PNA), or any DNA-like or RNA-like material of natural or synthetic origin. It will apparent to those of skill in the art that, when the nucleic acid is RNA, the deoxynucleotides A, G, C, and T are replaced by the ribonucleotides A, G, C, and U, respectively.

Any nucleic acid may be used in the present invention, given the presence of differently methylated CpG islands can be detected therein. The CpG island is a CpG-rich region in a nucleic acid sequence.

Methylation

In the present invention, any nucleic acid sample, in purified or nonpurified form, can be used, provided it contains or is suspected of containing a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten-fold relative to the rest of the genome. CpG islands have an average G*C content of about 60%, compared with the 40% average in bulk DNA. The islands take the form of stretches of DNA typically about one to two kilobases long. There are about 45,000 islands in the human genome.

In many genes, the CpG islands begin just upstream of a promoter and extend downstream into the transcribed region. Methylation of a CpG island at a promoter usually suppresses expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), downstream of coding regions in, for example, enhancer regions, and in introns.

Typically, the CpG-containing nucleic acid is DNA. However, the inventive method may employ, for example, samples that contain DNA, or DNA and RNA containing mRNA, wherein DNA or RNA may be single-stranded or double-stranded, or a DNA-RNA hybrid may be included in the sample.

A mixture of nucleic acids may also be used. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. Nucleic acids contained in a sample used for detection of methylated CpG islands may be extracted by a variety of techniques such as that described by Sambrook, et al. (Molecular Cloning: A Laboratory Manual, Cold Spring Harbor, N.Y., 1989).

Nucleic acids isolated from a subject are obtained in a biological sample from the subject. If it is desired to detect colorectal cancer or stages of colorectal cancer progression, the nucleic acid may be isolated from colon tissue by scraping or biopsy. Such samples may be obtained by various medical procedures known to those of skill in the art.

In one aspect of the invention, the state of methylation in nucleic acids of the sample obtained from a subject is hypermethylation compared with the same regions of the nucleic acid in a subject not having a cellular proliferative disorder of colon tissue. Hypermethylation as used herein refers to the presence of methylated alleles in one or more nucleic acids. Nucleic acids from a subject not having a cellular proliferative disorder of colon tissue contain no detectable methylated alleles when the same nucleic acids are examined.

Method for Detection of Methylation

Methylation-Specific PCR

When genomic DNA is treated with bisulfite, cytosine in the 5'-CpG'-3 region remains intact, if it was methylated, but the cytosine changes to uracil, if it was unmethylated. Accordingly, based on the base sequence converted after bisulfite treatment, PCR primer sets corresponding to a region having the 5'-CpG-3' base sequence are constructed. Herein, the constructed primer sets are two kinds of primer sets: a primer set corresponding to the methylated base sequence, and a primer set corresponding to the unmethylated base sequence. When genomic DNA is converted with bisulfite and then amplified by PCR using the above two kinds of primer sets, the PCR product is detected in the PCR mixture employing the primers corresponding to the methylated base sequence, if the genomic DNA was methylated, but the genomic DNA is detected in the PCR mixture employing the primers corresponding to the unmethylated, if the genomic DNA was unmethylated. This methylation can be quantitatively analyzed by agarose gel electrophoresis.

Real-Time Methylation Specific PCR

Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using a TanMan probe complementary to the amplified base sequence; and a method of detection using Sybergreen. Thus, the real-time methylation-specific PCR allows selective quantitative analysis of methylated DNA. Herein, a standard curve is plotted using an in vitro methylated DNA sample, and a gene containing no 5'-CpG-3' sequence in the base sequence is also amplified as a negative control group for standardization to quantitatively analyze the degree of methylation.

Pyrosequencing

The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

PCR Using Methylated DNA-Specific Binding Protein, Quantitative PCR, and DNA Chip Assay When a protein binding specifically only to methylated DNA is mixed with DNA, the protein binds specifically only to the methylated DNA. Thus, either PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA. Herein, the methylated DNA-specific binding protein may be, but not limited to, McrBt.

Detection of Differential Methylation-Methylation-Sensitive Restriction Endonuclease Detection of differential methylation can be accomplished by bringing a nucleic acid sample into contact with a methylation-sensitive restriction endonuclease that cleaves only unmethylated CpG sites.

In a separate reaction, the sample is further brought into contact with an isoschizomer of the methylation-sensitive restriction enzyme that cleaves both methylated and unmethylated CpG-sites, thereby cleaving the methylated nucleic acid.

Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

As used herein, the term "methylation-sensitive restriction enzyme" refers to a restriction enzyme (e.g., SmaI) that includes CG as part of its recognition site and has activity when the C is methylated as compared to when the C is not methylated. Non-limiting examples of methylation-sensitive restriction enzymes include MspI, HpaII, BssHII, BstUI and NotI. Such enzymes can be used alone or in combination. Examples of other methylation-sensitive restriction enzymes include, but are not limited to SacII and EagI.

The isoschizomer of the methylation-sensitive restriction enzyme is a restriction enzyme that recognizes the same recognition site as the methylation-sensitive restriction enzyme but cleaves both methylated and unmethylated CGs. An example thereof includes MspI.

Primers of the present invention are designed to be "substantially" complementary to each strand of the locus to be amplified and include the appropriate G or C nucleotides as discussed above. This means that the primers must be sufficiently complementary to hybridize with their respective strands under polymerization reaction conditions. Primers of the present invention are used in the amplification process, which is an enzymatic chain reaction (e.g., PCR) in which that a target locus exponentially increases through a number of reaction steps. Typically, one primer is homologous with the negative (−) strand of the locus (antisense primer), and the other primer is homologous with the positive (+) strand (sense primer). After the primers have been annealed to denatured nucleic acid, the nucleic acid chain is extended by an enzyme such as DNA Polymerase I (Klenow), and reactants such as nucleotides, and, as a result, + and − strands containing the target locus sequence are newly synthesized. When the newly synthesized target locus is used as a template and subjected to repeated cycles of denaturing, primer annealing, and extension, exponential synthesis of the target locus sequence occurs. The resulting reaction product is a discrete nucleic acid duplex with termini corresponding to the ends of specific primers employed.

The amplification reaction is PCR which is commonly used in the art. However, alternative methods such as real-time PCR or linear amplification using isothermal enzyme may also be used. In addition, multiplex amplification reactions may also be used.

Detection of Differential Methylation—Bisulfate Sequencing Method

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfite sequencing for detection of methylated nucleic acid.

Kit

The present invention provides a kit useful for the detection of a cellular proliferative disorder in a subject. The kit of the present invention comprises a carrier means compartmentalized to receive a sample therein, one or more containers comprising a second container containing PCR primers for amplification of a 5'-CpG-3' base sequence, and a third container containing a sequencing primer for pyrosequencing an amplified PCR product.

Carrier means are suited for containing one or more containers such as vials, tubes, and the like, each of the containers comprising one of the separate elements to be used in the method. In view of the description provided herein of the inventive method, those of skill in the art can readily determine the apportionment of the necessary reagents among the containers.

Substrates

After the target nucleic acid region has been amplified, the nucleic acid amplification product can be hybridized to a known gene probe attached to a solid support (substrate) to detect the presence of the nucleic acid sequence.

As used herein, the term "substrate", when used in reference to a substance, structure, surface or material, means a composition comprising a nonbiological, synthetic, nonliving, planar or round surface that is not heretofore known to comprise a specific binding, hybridization or catalytic recognition site or a plurality of different recognition sites or a number of different recognition sites which exceeds the number of different molecular species comprising the surface, structure or material. Examples of the substrate include, but are not limited to, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes silicon, silicates, glass, metals and ceramics; and wood, paper, cardboard, cotton, wool, cloth, woven and nonwoven fibers, materials and fabrics; and amphibious surfaces.

It is known in the art that several types of membranes have adhesion to nucleic acid sequences. Specific non-limiting examples of these membranes include nitrocellulose or other membranes used for detection of gene expression such as polyvinylchloride, diazotized paper and other commercially available membranes such as GENESCREEN™, ZETAPROBE™ (Biorad) and NYTRAN™. Beads, glass, wafer and metal substrates are also included. Methods for attaching nucleic acids to these objects are well known in the art. Alternatively, screening can be done in a liquid phase.

Hybridization Conditions

In nucleic acid hybridization reactions, the conditions used to achieve a particular level of stringency will vary depending on the nature of the nucleic acids being hybridized. For example, the length, degree of complementarity, nucleotide sequence composition (e.g., GC/AT content), and nucleic acid type (e.g., RNA/DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at room temperature (hybridization conditions); 0.2×SSC/0.1% SDS at room temperature (low stringency conditions); 0.2×SSC/0.1% SDS at 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary depending on the particular hybridization reaction involved, and can be determined empirically. In general, conditions of high stringency are used for the hybridization of the probe of interest.

Label

The probe of interest can be detectably labeled, for example, with a radioisotope, a fluorescent compound, a bioluminescent compound, a chemiluminescent compound, a metal chelator, or an enzyme. Appropriate labeling with such probes is widely known in the art and can be performed by any conventional method.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Discovery of Colorectal Cancer-Specific Methylated Genes

In order to screen biomarkers which are methylated specifically in colorectal cancer, 500 ng of each of genomic DNAs from 2 normal persons and genomic DNAs from the cancer tissue and adjacent normal tissue from 12 colorectal cancer patients was sonicated (Vibra Cell, SONICS), thus constructing about 200-300-bp-genomic DNA fragments.

To obtain only methylated DNA from the genomic DNA, a methyl binding domain (Methyl binding domain; MBD) (Fraga et al., *Nucleic Acid Res.*, 31: 1765, 2003) known to bind to methylated DNA was used. Specifically, 2 μg of 6×His-tagged MBD2bt was pre-incubated with 500 ng of the genomic DNA of *E. coli* JM110 (No. 2638, Biological Resource Center, Korea Research Institute of Bioscience & Biotechnology), and then bound to Ni-NTA magnetic beads (Qiagen, USA). 500 ng of each of the sonicated genomic DNAs isolated from the normal persons and the colorectal cancer patient patients was allowed to react with the beads in the presence of binding buffer solution (10 mM Tris-HCl (pH 7.5), 50 mM NaCl, 1 mM EDTA, 1 mM DTT, 3 mM $MgCl_2$, 0.1% Triton-X100, 5% glycerol, 25 mg/ml BSA) at 4° C. for 20 minutes. Then, the beads were washed three times with 500 μL of a binding buffer solution containing 700 mM NaCl, and then methylated DNA bound to the MBD2bt was isolated using the QiaQuick PCR purification kit (Qiagen, USA).

Then, the methylated DNAs bound to the MBD2bt were amplified using a genomic DNA amplification kit (Sigma, USA, Cat. No. WGA2), and 4 μg of the amplified DNAs were labeled with Cy5 using a BioPrime Total Genomic Labeling system I (Invitrogen Corp., USA). To indirectly compare the degree of methylation between the normal person and the colorectal cancer patient, a reference DNA was constructed. Herein, the reference DNA was constructed by mixing the genomic DNAs from the 12 colorectal cancer patients with each other in the same amount, amplifying the genomic DNA mixture using a genomic DNA amplification kit (Sigma, USA, Cat. No. WGA2), and labeling 4 μg of the amplified genomic DNA with Cy3 using a BioPrime Total Genomic Labeling system I (Invitrogen Corp., USA). The reference DNA was mixed with each of the DNAs of the normal persons and the colorectal cancer patients, and then hybridized to 244K human CpG microarrays (Agilent, USA) (see FIG. 1). After the hybridization, the DNA mixture was subjected to a series of washing processes, and then scanned using an Agilent scanner. The calculation of signal values from the microarray images was performed by calculating the relative difference in signal strength between the normal person sample and the colorectal cancer patient sample using Feature Extraction program v. 9.5.3.1 (Agilent).

Figure 2:
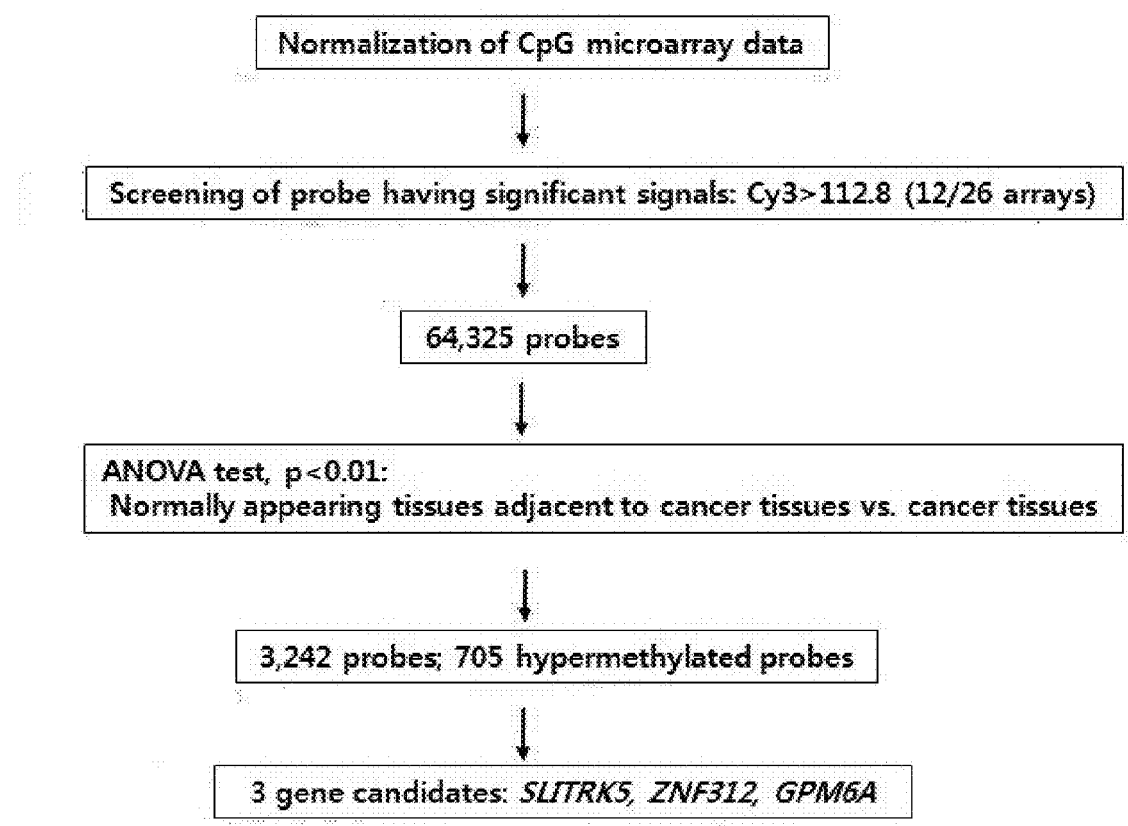
FIG. 2 is a schematic diagram showing a process of screening colorectal cancer-specific hypermethylated genes from the CpG microarray data of colorectal cancer.

In order to screen probes having reliable hybridization signals, 64,325 probes having a Cy3 signal value of more than 112.8 in at least 21 arrays among a total of 26 arrays were screened by the cross gene error model using GeneSpring 7.3 program (Agilent, USA). In order to screen probes hypermethylated specifically in colorectal cancer from the above probes, the normally appearing tissue adjacent to the colorectal cancer tissue and the colorectal cancer tissue are compared with each other, and in order to screen probes showing differential methylation, the ANOVA test was performed, thereby screening 3,242 probes ($p<0.01$). From these probes, 705 probes hypermethylated in the colorectal cancer tissue were further screened, and from these probes, 3 biomarker gene candidates (SLITRK5, ZNF312, GPM6A) showing hypermethylation in two or more adjacent probes present within a distance of about 400 bp were selected (see FIG. 2).

The 4 biomarker candidate genes analyzed using the above analysis method were listed in Table 1 below. In addition, the nucleotide sequence corresponding to the probe of each of the 4 genes showing hypermethylation in the CpG microarray was analyzed using MethPrimer (http://itsa.ucsf.edu/~urolab/methprimer/index1.html), thereby confirming CpG islands in the probes.

TABLE 1

List of methylation biomarker candidate genes for colorectal cancer diagnosis

| Candidate genes | Probe locations [a] | GenBank No. | Description |
|---|---|---|---|
| SLITRK5 | +1,811, +2,046 | NM_015567 | SLIT and NTRK-like family, member 5 |
| ZNF312 | +2,558, +2,646 | NM_018008 | zinc finger protein 312 |
| GPM6A | +554, +786 | NM_005277 | Glycoprotein M6A |

[a] base pairs (bp) from the transcription start site (+1)

Example 2

Measurement of Methylation of Biomarker Genes in Cancer Cell Lines

In order to additionally confirm the methylation state of the biomarker candidate genes selected in Example 1, pyrosequencing for the promoter and intron region of each gene was performed.

In order to modify unmethylated cytosine to uracil using bisulfite, total genomic DNA was isolated from each of the colorectal cancer cell lines Caco-2 (KCLB No. 30037.1) and HCT116 (KCLB No. 10247), and 200 ng of the genomic DNA was treated with bisulfite using the EZ DNA methylation-gold kit (Zymo Research, USA). When the DNA was treated with bisulfite, unmethylated cytosine was modified to uracil, and the methylated cytosine remained without changes. The DNA treated with bisulfite was eluted in 20 μl of sterile distilled water and subjected to pyrosequencing.

PCR and sequencing primers for performing pyrosequencing for the 3 genes were designed using PSQ assay design program (Biotage, USA). The PCR and sequencing primers for measuring the methylation of each gene are shown in Tables 2 and 3 below.

TABLE 2

| | | | PCR primers | | |
|---|---|---|---|---|---|
| Genes | Primers | Sequences (5' 3') [a] | SEQ ID NOS | CpG location [b] | Size of amplicon (bp) |
| SLITRK5 | forward | TGTTGATTTTTGGTGTA TTGA | 7 | +1949, +1960, +1963, +1989 | 253 |
| | reverse | AACACATCAACRTCCTA ATTACATA | 8 | | |

TABLE 2-continued

PCR primers

| Genes | Primers | Sequences (5' 3')[a] | SEQ ID NOS | CpG location[b] | Size of amplicon (bp) |
|---|---|---|---|---|---|
| ZNF312 | forward | TGTTTGGTGTAGGGGGA AGT | 9 | +2521, +2527, +2535, +2546 | 224 |
| | reverse | CCCRAAAAAATTATTTT ACCTCCA | 10 | | |
| GPM6A | forward | GGGAAATAAAGAAAGAT TAAGAGA | 11 | +560, +567, +572, +598 | 121 |
| | reverse | ACCCCRTTTCAACTTAC TC | 12 | | |

[a] Y = C or T; R = A or G
[b] distances (nucleotides) from the transcription start site (+1): the positions of CpG regions on the genomic DNA used in the measurement of methylation

TABLE 3

Sequences of sequencing primers for methylation marker genes

| Genes | Sequences (5' --> 3')[a] | SEQ ID NOS |
|---|---|---|
| SLITRK5 | ATTTTAGTGGTTTAAAGATG | 13 |
| GPM6A | AAGATTAAGAGATTTAGGAT | 15 |

[a] Y = C or T; R = A or G 20 ng of the genomic DNA treated with bisulfite was amplified by PCR. In the PCR amplification, a PCR reaction solution (20 ng of the genomic DNA treated with bisulfite, 5 μl of 10×PCR buffer (Enzynomics, Korea), 5 units of Taq polymerase (Enzynomics, Korea), 4 μl of 2.5 mM dNTP (Solgent, Korea), and 2 μl (10 pmole/μl) of PCR primers) was used, and the PCR reaction was performed under the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index. The methylation index was calculated by determining the average rate of cytosine binding to each CpG island.

Figure 3:
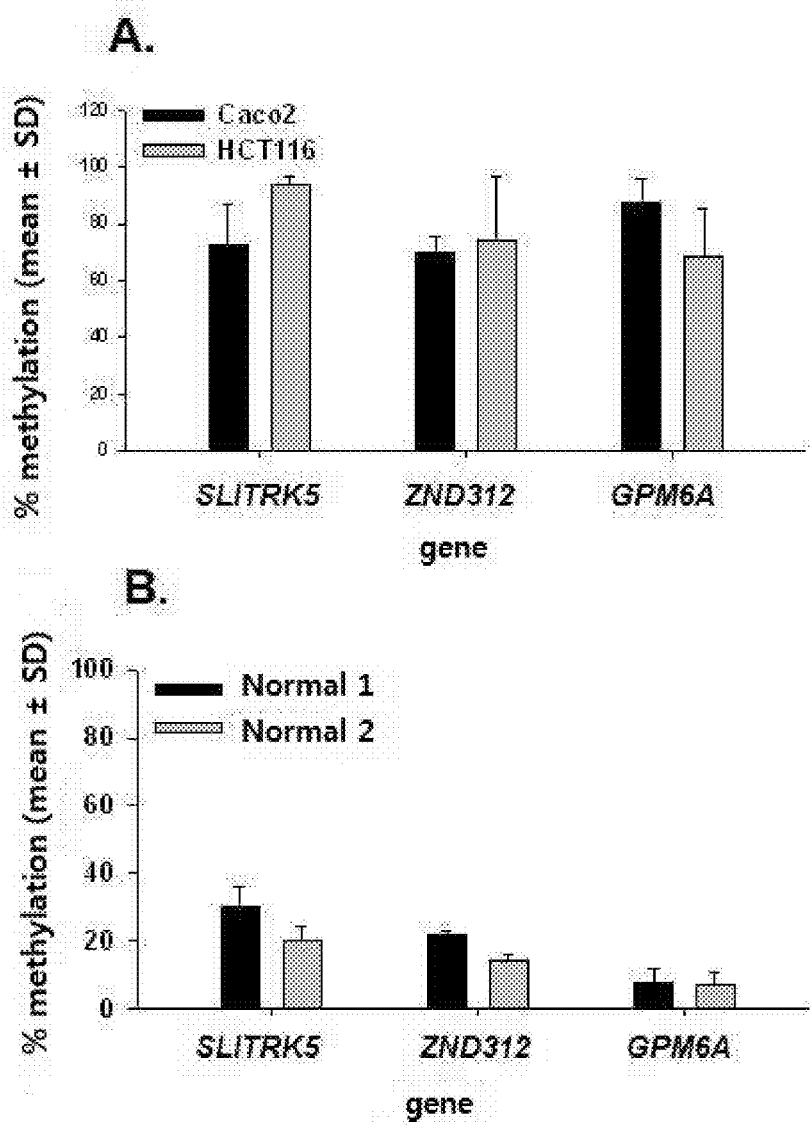
FIG. 3 is a graphic diagram showing the results of measuring the degree of methylation of 3 biomarker candidate genes in a colorectal cancer cell line and the colon tissues of normal persons by pyrosequencing.

As described above, the degrees of methylation of the biomarker candidate genes in the colorectal cancer cell lines were measured using the pyrosequencing method. As a result, as can be seen in FIG. 3A, the 3 marker genes were all methylated at high levels of 50% in at least one of the cell lines. The 3 genes showed high levels of methylation in the colorectal cancer cell lines, suggesting that these genes are useful as biomarkers for colorectal cancer diagnosis. In order to verify whether these genes are used as biomarkers, the following test was additionally performed using a tissue sample.

Example 3

Measurement of Methylation of Biomarker Candidate Genes in Colon Tissue of Normal Persons In order for the 3 biomarker candidate gene to have utility as biomarkers for colorectal cancer diagnosis, these genes should show low levels of methylation in the colon tissue of normal persons other than patients, but should show high levels of methylation in colorectal cancer tissue.

To verify whether these genes satisfy these requirements, genomic DNA was isolated from two normal person's colorectal tissues (Biochain) using the QIAamp DNA mini-kit (QIAGEN, USA), and 200 ng of the isolated genomic DNA was treated with bisulfite using the EZ DNA methylation-gold kit (Zymo Research, USA). The treated DNA was eluted in 20 μl of sterile distilled water and subjected to pyrosequencing.

20 ng of the genomic DNA treated with bisulfite was amplified by PCR. In the PCR amplification, a PCR reaction solution (20 ng of the genomic DNA treated with bisulfite, 5 μl of 10×PCR buffer (Enzynomics, Korea), 5 units of Taq polymerase (Enzynomics, Korea), 4 μl of 2.5 mM dNTP (Solgent, Korea), and 2 μl (10 pmole/μl) of PCR primers) was used, and the PCR reaction was performed under the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index thereof. The methylation index was calculated by determining the average rate of cytosine binding to each CpG region.

As a result, as can be seen in FIG. 3B, the GPM6A gene among the 3 genes showed the lowest methylation level in the normal tissue. Thus, in order to verify whether the GPM6A gene is useful as a biomarker, the following test was performed using the tissue of colorectal cancer patients.

Example 4

Measurement of Methylation of Biomarker Genes in Tissue of Colorectal Cancer Patients In order to verify whether the GPM6A gene showing low level of methylation in the colon tissue of normal persons is useful as a biomarker for colorectal cancer diagnosis, genomic DNAs were isolated from colorectal cancer tissues isolated from 96 colorectal cancer patients (the Biochip Research Center in Yonsei University, appointed by the Korean Ministry of Health and Welfare) and the normally appearing tissues adjacent thereto.

200 ng of each of the isolated genomic DNAs was treated with bisulfite using the EZ DNA methylation-gold kit (Zymo Research, USA). Each of the treated DNAs was eluted in 20 µl of sterile distilled water and subjected to pyrosequencing.

20 ng of the genomic DNA treated with bisulfite was amplified by PCR. In the PCR amplification, a PCR reaction solution (20 ng of the genomic DNA treated with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction solution was performed under the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system. After the pyrosequencing, the methylation degree of the DNA was measured by calculating the methylation index thereof. The methylation index was calculated by determining the average rate of cytosine binding to each CpG region.

Figure 4:
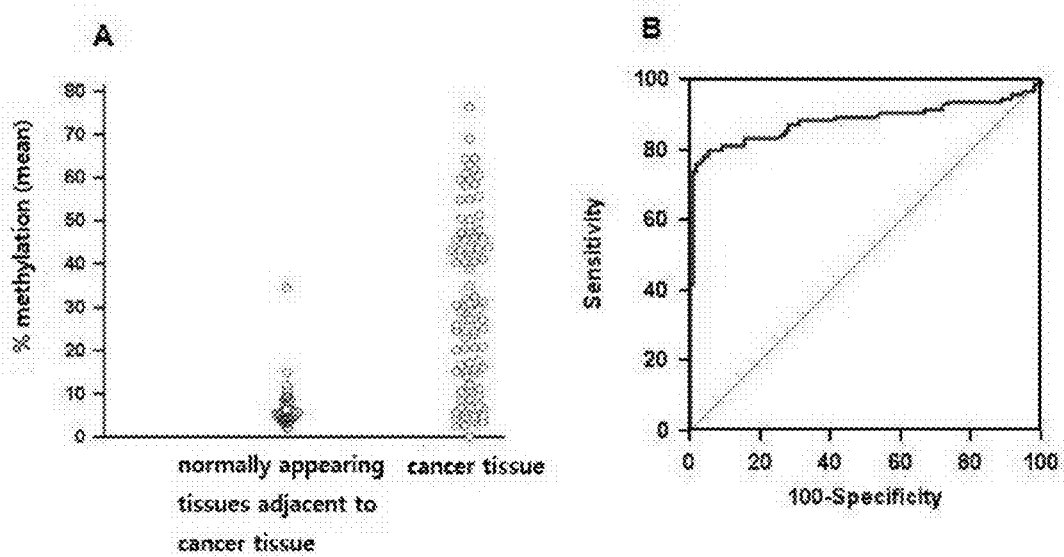
FIG. 4 is a graphic diagram showing the results of measuring the degrees of methylation of GPM6A methylation biomarker in colorectal cancer tissue and adjacent normal tissue by pyrosequencing, and the results of measuring the sensitivity and specificity of GPM6A methylation biomarker for colorectal cancer by ROC curve analysis.

The degree of methylation of the GPM6A gene was measured. As a result, as can be seen in FIG. 4A, the GPM6A gene showed higher levels of methylation in the colorectal cancer tissues of 72 patents (80.2%) of the 96 patients compared to those in the normally appearing tissues. Table 4 below shows the average values of the methylation levels of the GPM6A biomarker gene in the colorectal cancer tissues and the normally appearing tissues adjacent thereto. In order to confirm whether the level of methylation of the genes statistically significantly differs between the colorectal cancer tissue and the normally appearing tissue, the Chi-Square test was performed. As a result, it could be seen that all the three genes showed statistically significant levels (p<0.01) (see Table 4).

TABLE 4

Results of quantitative analysis of methylation of GPM6A biomarker

| Average methylation level (%, average ± standard deviation) | | |
|---|---|---|
| Normally appearing tissues | Colorectal cancer tissues | P values [a] |
| 6.8 ± 5.7 | 30.3 ± 19.6 | <0.0001 |

[a] p values obtained through the Chi-Square test

Example 5

Evaluation of the Ability of GPM6A Biomarker to Diagnose Colorectal Cancer

For the GPM6A gene confirmed to be useful as colorectal cancer markers in Example 4, receiver operating characteristic (ROC) analysis was performed using MedCalc program (MEDCALC, Belgium) in order to evaluate the ability of the genes to diagnose colorectal cancer.

As a result, as shown in FIG. 4B, the sensitivity and specificity of the GPM6A gene for colorectal cancer were, respectively, 80.2% and 94.8%. This suggests that the GPM6A gene has a very excellent ability to diagnose colorectal cancer. Table 5 shows the results of ROC curve analysis of the GPM6A gene for colorectal cancer diagnosis.

TABLE 5

Results of ROC curve analysis for colorectal cancer diagnosis of the GPM6A methylation biomarker gene

| | |
|---|---|
| AUC (95% C.I) | 0.884 (0.830-0.926) |
| Cut-off[a] | >10.31 |
| p value | 0.0001 |
| Sensitivity (%) (95% C.I) | 80.2 (70.8-87.6) |
| Specificity (%) (95% C.I) | 94.8 (88.3-98.3) |

[a] methylation index critera for distinction between normal and cancer samples

Additionally, the GPM6A gene was evaluated for its ability to diagnose colorectal cancer in a fecal sample.

Figure 5:
FIG. 5 shows the results of verifying the methylation of a GPM6A biomarker gene in the fecal tissues of normal persons and colorectal cancer patients by methylation-specific PCR.
Figure 5:

Specifically, measurement of the methylation was performed on two kinds of colorectal cancer cell lines using a nested methylation-specific PCR (MSP) technique, and it was confirmed that all the two kinds of colorectal cancer cell lines were methylated as shown in FIG. 5A. This result is identical to the result of pyrosequencing performed in the above Example 2. Genomic DNAs were isolated from the fecal samples of 4 normal persons and 8 colorectal cancer patients (the Biochip Research Center in Yonsei University, appointed by the Korean Ministry of Health and Welfare). 4 µg of each of the isolated genomic DNAs was treated with bisulfite using the EZ DNA methylation-gold kit (Zymo Research, USA). Each of the treated DNAs was eluted in 20 µl of sterile distilled water and subjected to a nested MSP test. The primer sequences used in the nested MSP test are shown in Table 6 below.

TABLE 6

Primer sequences used in MSP test of GPM6A gene

| Methylation | Primers | Primer sequences (5' --> 3') | Size of amplified product (bp) | SEQ ID NOS |
|---|---|---|---|---|
| Methylation | Outer-F | TTAAAAGGGCGTTTATATTGGTTCG | 233 | 16 |
| | Outer-R | CCTCGCTCTTCGAAATAACTCGTA | | 17 |
| | Inner-F | TAGGGTTCGTTTATTCGGTGTTTAGC | 156 | 18 |
| | Inner-R | CCTCGCTCTTCGAAATAACTCGTA | | 19 |
| Non-methylation | Outer-F | TAAAAGGGTGTTTATATTGGTTTGG | 233 | 20 |
| | Outer-R | CCCTCACTCTTCAAAATAACTCATA | | 21 |
| | Inner-F | GGTAGGGTTTGTTTATTTGGTGTTTAGTG | 160 | 22 |
| | Inner-R | TCCCTCACTCTTCAAAATAACTCATA | | 23 |

1 μg of the genomic DNA treated with bisulfite was amplified by PCR. In the PCR amplification, a PCR reaction solution (20 μg of the genomic DNA treated with bisulfite, 5 μl of 10×PCR buffer (Enzynomics, Korea), 5 units of Taq polymerase (Enzynomics, Korea), 4 μl of 2.5 mM Dntp (Solgent, Korea), and 2 μl (10 pmole/μl) of PCR primers) was used, and the PCR reaction was performed under the following conditions: predenaturation at 95° C. for 5 min, and then 30 cycles of denaturation at 95° C. for 40 sec, annealing at 60° C. for 45 sec and extension at 72° C. for 40 sec, followed by final extension at 72° C. for 5 min. ½ of the PCR product was taken and amplified by PCR for 45 cycles in the same manner as above. The amplification of the PCR products was confirmed by electrophoresis on 2.0% agarose gel.

As a result, as shown in FIG. 5B, it was observed that the GPM6A gene was not methylated in the tissues of the 4 normal persons, but was methylated in 5 (62.5%) of the 8 colorectal cancer patients. This suggests that the GPM6A gene is useful for the diagnosis of colorectal cancer in feces.

INDUSTRIAL APPLICABILITY

As described above, the present invention enables the methylation of the CpG island of a colorectal cancer-specific marker gene to be detected to thereby provide information for diagnosing colorectal cancer. The use of the inventive method for detecting methylation and the inventive composition, kit and nucleic acid chip for diagnosing colorectal cancer makes it possible to diagnose colorectal cancer at an early transformation stage, thus enabling the early diagnosis of colorectal cancer. In addition, the inventive method enables colorectal cancer to be effectively diagnosed in an accurate and rapid manner compared to conventional methods.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

SEQUENCING LISTING FREE TEXT

Electronic file is attached.

What is claimed is:

1. A method for detecting CpG methylation of GPM6A (glycoprotein M6A) gene, the method comprising the steps of:
    (a) isolating genomic DNA from a clinical sample of a human subject selected from the group consisting of colorectal tissue, feces, urine, serum, and blood plasma;
    (b) treating the genomic DNA or a fragment thereof with bisulfite, wherein the genomic DNA or fragment thereof is treated with bisulfite in such a way that cytosine is converted into a base that is different in its base-pairing behavior in the DNA duplex; and
    (c) determining hypermethylation of the CpG of the promoter or the CpG of the first intron of GPM6A gene in the genomic DNA or fragment thereof treated with bisulfite according to step (b) with primers selected from the group consisting of SEQ ID NOS: 16 to 19.

2. The method of claim 1, wherein the detection of hypermethylation is performed by a method selected from the group consisting of PCR, methylation-specific PCR, real-time methylation-specific PCR, PCR assay using a methylation DNA-specific binding protein, quantitative PCR, DNA chip-based assay, pyrosequencing, and bisulfite sequencing.

3. The method of claim 1, wherein step (c) is performed by detecting the hypermethylation of the CpG island of the promoter of GPM6A.

4. The method of claim 1, wherein the clinical sample is colorectal tissue.

5. The method of claim 1, wherein the clinical sample is feces.

6. The method of claim 1, wherein the clinical sample is urine.

7. The method of claim 1, wherein the clinical sample is serum.

8. The method of claim 1, wherein the clinical sample is blood plasma.

9. The method of claim 1, wherein step (c) is performed by detecting the hypermethylation of the CpG island of the first intron of GPM6A.

10. The method of claim 9, wherein the first intron of GPM6A gene is SEQ ID NO: 1.

* * * * *

SEQUENCE LISTING

```
<160> NUMBER OF SEQ ID NOS: 23

<210> SEQ ID NO 1
<211> LENGTH: 700
<212> TYPE: DNA
<213> ORGANISM: Homo sapiens

<400> SEQUENCE: 1
ggtctaccgt gctgggggcg gtatttggga aataaagaaa gactaagaga cccaggatcc      60
gaatagcgag gcgattacag ggagatctct gtcctcccga gttcccacgt tttcatgttc     120
tctttgggga gcaagttgaa acggggcacg agaaatggaa acttcctaaa acttccactt     180
tgtacaggtt tgagcagagg aaggtgctgg tgcagggcca gactggggac aatttctagt     240
```

-continued

```
cccttttccaa acgaagtgcc catttgcaca aaaggtttga ggttgaggct gaaggctgat    300
tcttcctaaa ttccacctgg gtaaacagcg tgattaaaag ggcgtccaca ctggctcggg    360
tcactggacg gtggagttcg gcgcagttca gcttcgctca agtttccagg cagggtccgc    420
ttattcggtg cttagcggag gcagcttgga atagctccag gaatgtgact gcgtgtggcg    480
gaggggagga agaactgggt gtgaaatagc cgattcacac ccagcactag gacgcagggt    540
cccacgagtc acctcgaaga gcgagggaga agctggggag gagaaagcac tcgccatccc    600
tggactggcg tatccacagg cgcaggggag atgctgctct tccgcggttg ccgactgcgt    660
tcagcccgca gcccgagtta ctcttccaac cccagcccgc                           700
```

<210> SEQ ID NO 2  
<211> LENGTH: 20  
<212> TYPE: DNA  
<213> ORGANISM: Artificial  
<220> FEATURE:  
<223> OTHER INFORMATION: probe

<400> SEQUENCE: 2

```
gtatttggga aataaagaaa                                                  20
```

<210> SEQ ID NO 3  
<211> LENGTH: 30  
<212> TYPE: DNA  
<213> ORGANISM: Artificial  
<220> FEATURE:  
<223> OTHER INFORMATION: probe

<400> SEQUENCE: 3

```
gactaagaga cccaggatcc gaatagcgag                                       30
```

<210> SEQ ID NO 4  
<211> LENGTH: 40  
<212> TYPE: DNA  
<213> ORGANISM: Artificial  
<220> FEATURE:  
<223> OTHER INFORMATION: probe

<400> SEQUENCE: 4

```
gttcccacgt tttcatgttc tctttgggga gcaagttgaa                            40
```

<210> SEQ ID NO 5  
<211> LENGTH: 50  
<212> TYPE: DNA  
<213> ORGANISM: Artificial  
<220> FEATURE:  
<223> OTHER INFORMATION: probe

<400> SEQUENCE: 5

```
ggcgtccaca ctggctcggg tcactggacg gtggagttcg gcgcagttca                 50
```

<210> SEQ ID NO 6  
<211> LENGTH: 60  
<212> TYPE: DNA  
<213> ORGANISM: Artificial  
<220> FEATURE:  
<223> OTHER INFORMATION: probe

<400> SEQUENCE: 6

```
agtttccagg cagggtccgc ttattcggtg cttagcggag gcagcttgga atagctccag      60
```

<210> SEQ ID NO 7

```
<211> LENGTH: 21
<212> TYPE: DNA
<213> ORGANISM: Artificial
<220> FEATURE:
<223> OTHER INFORMATION: primer

<400> SEQUENCE: 7
tgttgatttt tggtgtattg a                                                 21

<210> SEQ ID NO 8
<211> LENGTH: 25
<212> TYPE: DNA
<213> ORGANISM: Artificial
<220> FEATURE:
<223> OTHER INFORMATION: primer

<400> SEQUENCE: 8
aacacatcaa crtcctaatt acata                                             25

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
tgtttggtgt aggggaagt                                                    20

<210> SEQ ID NO 10
<211> LENGTH: 24
<212> TYPE: DNA
<213> ORGANISM: Artificial
<220> FEATURE:
<223> OTHER INFORMATION: primer

<400> SEQUENCE: 10
cccraaaaaa ttattttacc tcca                                              24

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
gggaaataaa gaaagattaa gaga                                              24

<210> SEQ ID NO 12
<211> LENGTH: 19
<212> TYPE: DNA
<213> ORGANISM: Artificial
<220> FEATURE:
<223> OTHER INFORMATION: primer

<400> SEQUENCE: 12
accccrtttc aacttactc                                                    19

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
```

```
atttagtgg tttaaagatg                                          20

<210> SEQ ID NO 14
<211> LENGTH: 19
<212> TYPE: DNA
<213> ORGANISM: Artificial
<220> FEATURE:
<223> OTHER INFORMATION: primer

<400> SEQUENCE: 14
tgggtgtatt gagagattt                                           19

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
aagattaaga gatttaggat                                          20

<210> SEQ ID NO 16
<211> LENGTH: 25
<212> TYPE: DNA
<213> ORGANISM: Artificial
<220> FEATURE:
<223> OTHER INFORMATION: primer

<400> SEQUENCE: 16 ttaaagggc gtttatattg gttcg                                     25

<210> SEQ ID NO 17
<211> LENGTH: 24
<212> TYPE: DNA
<213> ORGANISM: Artificial
<220> FEATURE:
<223> OTHER INFORMATION: primer

<400> SEQUENCE: 17
cctcgctctt cgaaataact cgta                                     24

<210> SEQ ID NO 18
<211> LENGTH: 26
<212> TYPE: DNA
<213> ORGANISM: Artificial
<220> FEATURE:
<223> OTHER INFORMATION: primer

<400> SEQUENCE: 18
tagggttcgt ttattcggtg tttagc                                   26

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
cctcgctctt cgaaataact cgta                                     24

<210> SEQ ID NO 20
<211> LENGTH: 25
<212> TYPE: DNA
```

```
<213> ORGANISM: Artificial
<220> FEATURE:
<223> OTHER INFORMATION: primer

<400> SEQUENCE: 20
taaaagggtg tttatattgg tttgg                                          25

<210> SEQ ID NO 21
<211> LENGTH: 25
<212> TYPE: DNA
<213> ORGANISM: Artificial
<220> FEATURE:
<223> OTHER INFORMATION: primer

<400> SEQUENCE: 21
ccctcactct tcaaaataac tcata                                          25

<210> SEQ ID NO 22
<211> LENGTH: 29
<212> TYPE: DNA
<213> ORGANISM: Artificial
<220> FEATURE:
<223> OTHER INFORMATION: primer

<400> SEQUENCE: 22
ggtagggttt gtttatttgg tgtttagtg                                      29

<210> SEQ ID NO 23
<211> LENGTH: 26
<212> TYPE: DNA
<213> ORGANISM: Artificial
<220> FEATURE:
<223> OTHER INFORMATION: primer

<400> SEQUENCE: 23
tccctcactc ttcaaaataa ctcata                                         26
```